US00PP31231P2

(12) United States Plant Patent
Wheeler et al.

(10) Patent No.: US PP31,231 P2
(45) Date of Patent: Dec. 17, 2019

(54) BLUEBERRY PLANT NAMED 'BB05-35FL-10'

(50) Latin Name: *Vaccinium corymbosum.*
Varietal Denomination: BB05-35FL-10

(71) Applicant: Berry Blue, LLC, Grand Junction, MI (US)

(72) Inventors: Edmund J. Wheeler, Holland, MI (US); James F. Hancock, Scarborough, ME (US)

(73) Assignee: Berry Blue, LLC, Grand Junction, MI (US)

( * ) Notice: Subject to any disclaimer, the term of this patent is extended or adjusted under 35 U.S.C. 154(b) by 0 days.

(21) Appl. No.: 16/350,444

(22) Filed: Nov. 15, 2018

(51) Int. Cl.
*A01H 5/08* (2018.01)
*A01H 6/00* (2018.01)

(52) U.S. Cl.
USPC ..... Plt./157
CPC ..... *A01H 6/00* (2018.05)

(58) Field of Classification Search
USPC ..... Plt./157
See application file for complete search history.

*Primary Examiner* — Anne Marie Grunberg
(74) *Attorney, Agent, or Firm* — King IP Law; Joshua King

(57) ABSTRACT

'BB05-35FL-10' is a new and distinct low chill tetraploid, Southern highbush blueberry (*Vaccinium*) variety. Plants of 'BB05-35FL-10' are very vigorous with a medium upright bush habit and a medium number of upright canes and lateral branches. Bush crown size is medium and leafing and growth are excellent. The berries are firm, medium crunchy in texture with a pleasing balanced flavor of sweetness and acidity and have storage ability of two to three weeks. In general, the productivity has been outstanding in Florida, Georgia USA, and Chile with high yields.

5 Drawing Sheets

Latin name of the genus and species of the plant claimed: *Vaccinium corymbosum.*

Variety denomination: BLUEBERRY PLANT NAMED 'BB05-35FL-10'.

BACKGROUND AND SUMMARY

Blueberries are a well-known fruit enjoyed by many throughout the world. One example of an existing, patented blueberry variety is 'Springhigh', U.S. Plant Pat. No. 16,404. Another example of an existing, patented blueberry variety is 'Star', U.S. Plant Pat. No. 10,675.

Comparing 'BB05-35FL-10' to 'Springhigh', the berry weight of 'BB05-35FL-10' is much heavier, the soluble solids are greater, the titratable acidity is less, the ripe fruit is much firmer, and the date of bloom is one week earlier.

Comparing 'BB05-35FL-10' to 'Star', the 50% ripening date of 'BB05-35FL-10' is 5 days earlier and 'BB05-35FL-10' has a much larger and flatter shaped berry.

The present cultivar, 'BB05-35FL-10', provides one or more advantages over existing varieties.

BRIEF DESCRIPTION OF THE PHOTOGRAPHS

DETAILED DESCRIPTION

Figure 1:
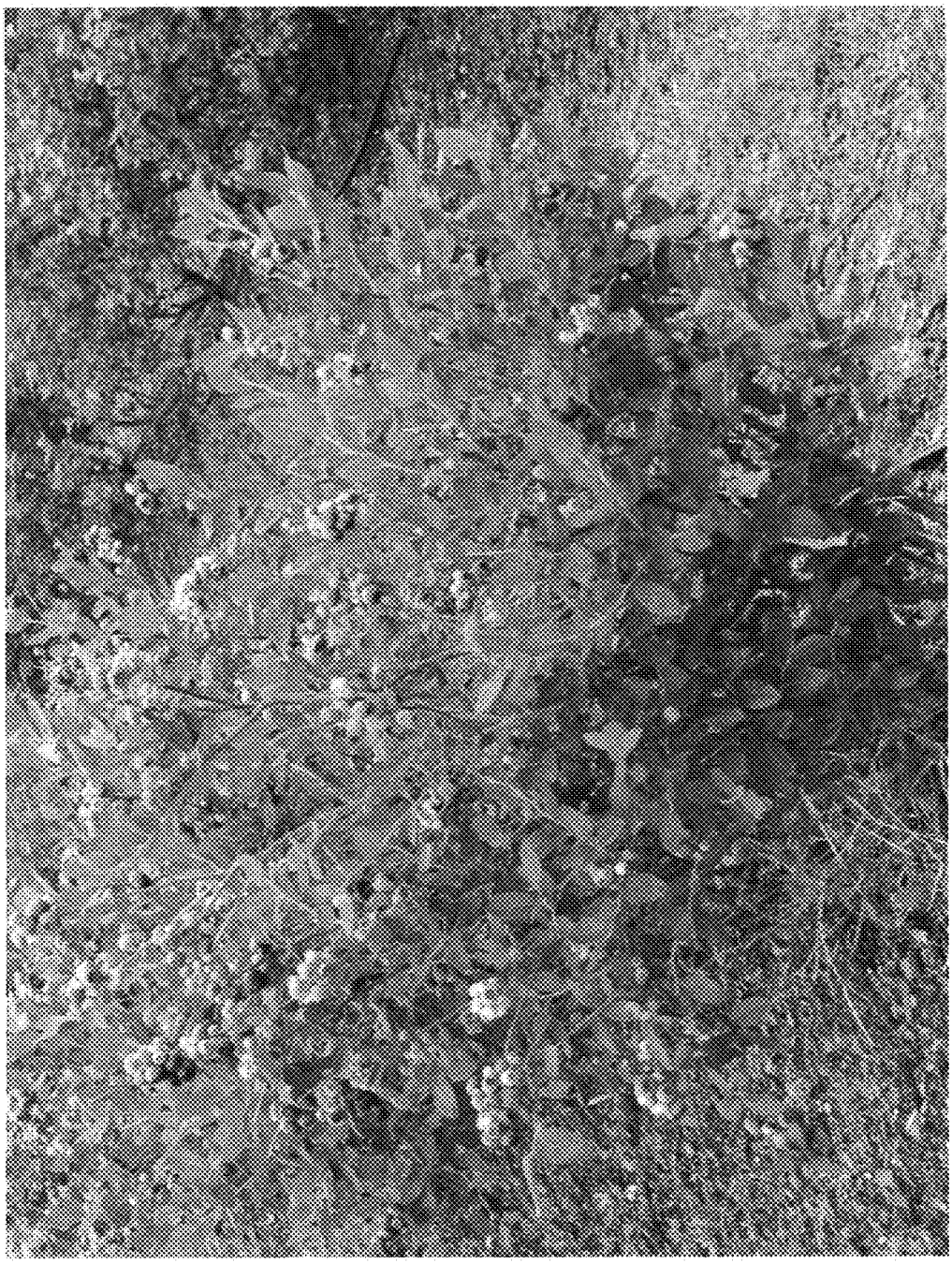
FIG. 1 is a photograph of the Blueberry cultivar 'BB05-35FL-10' taken May 2018 at Interlachen, Fla., showing the overall bush habit, both ripe and unripe fruit, fruit cluster density, fruit load, leaf color and the cane number and arrangement.
Figure 2:
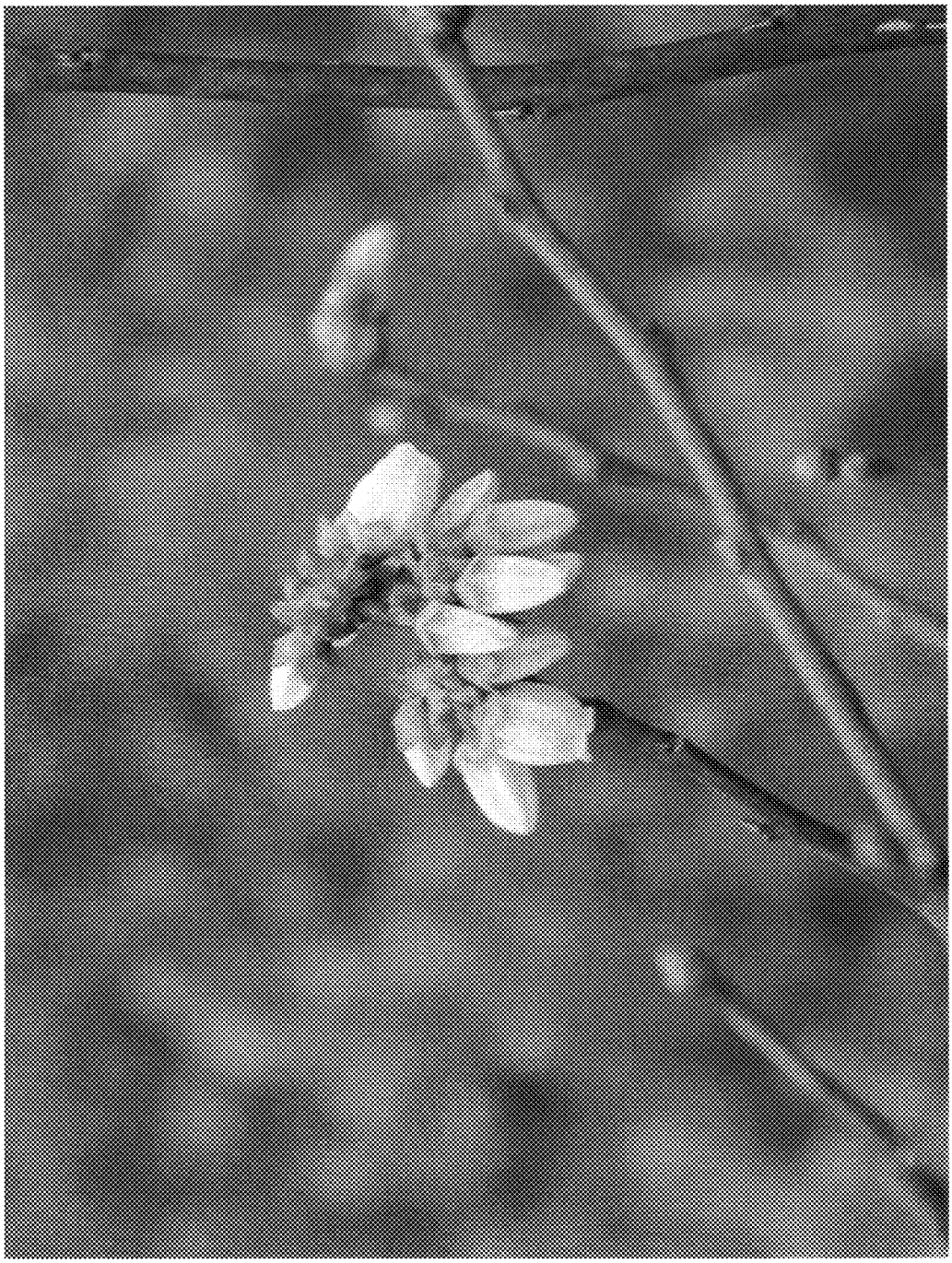
FIG. 2 is a close-up photograph of the Blueberry cultivar 'BB05-35FL-10' taken January 2018 at Interlachen, Fla., showing open and unopened flowers and their number, color, size and shape, and the winter color of one-year old canes.
Figure 3:
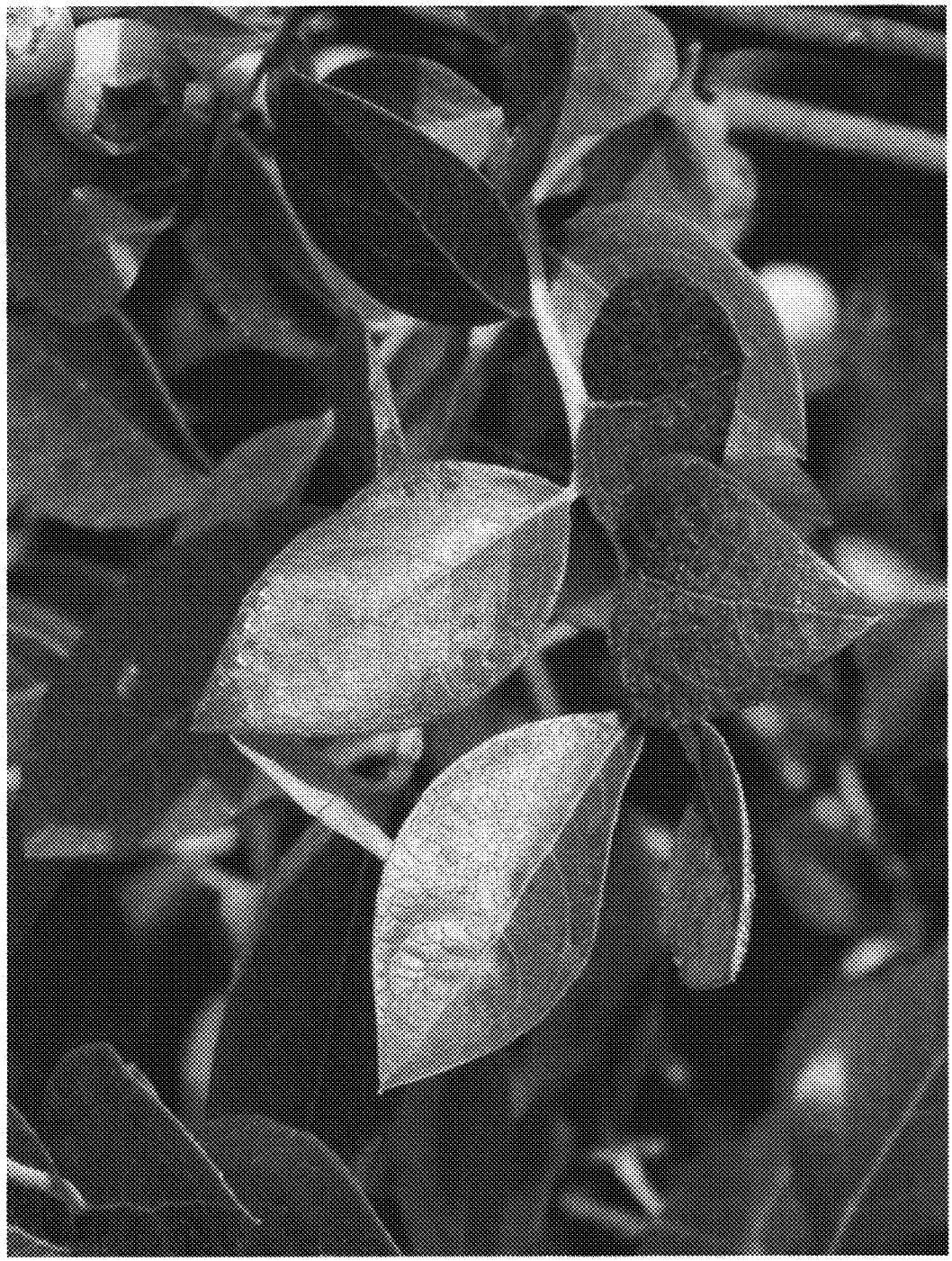
FIG. 3 is a close-up photograph of the Blueberry cultivar 'BB05-35FL-10' taken May 2018 at Interlachen, Fla., showing mature leaves, their color, relative size, arrangement and shape, and summer color of immature canes.
Figure 4:
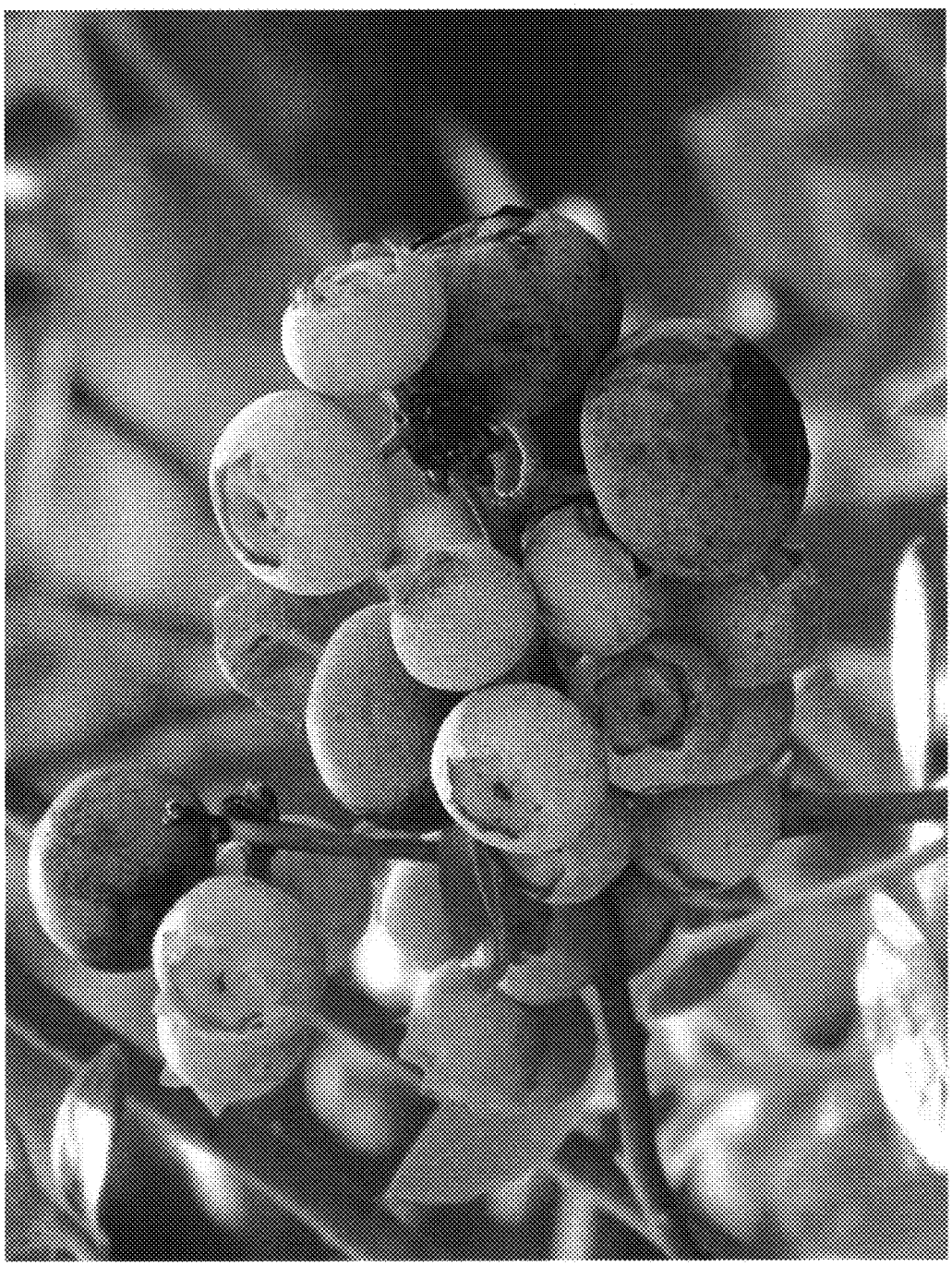
FIG. 4 is a close-up photograph of the Blueberry cultivar 'BB05-35FL-10' taken May 2018 at Interlachen, Fla., showing ripe and unripe fruit, their color and shape, calyx diameter and depth, cluster density and mature summer color of canes.
Figure 5:
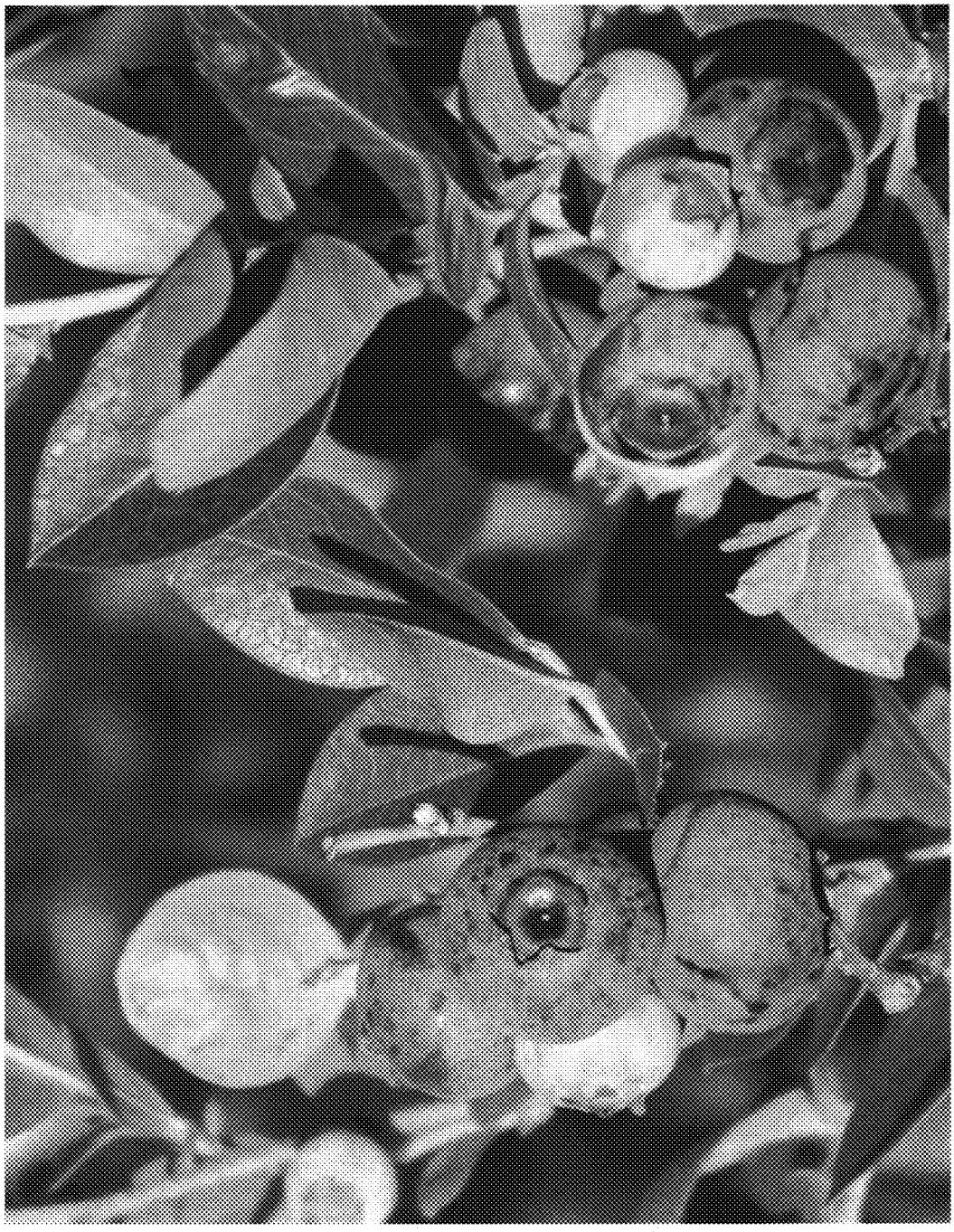
FIG. 5 is a close-up photograph of the Blueberry cultivar 'BB05-35FL-10' taken May 2018 at Interlachen, Fla., showing ripe and unripe fruit, their shape and color, the shape and size of the berry calyx, cluster density, and mature and immature leaves.

Note: statements of characteristics herein represent exemplary observations of the cultivar herein and will vary depending on time of year, location, annual weather, etc. Where dimensions, sizes, colors, and other characteristics are given, it is to be understood that such characteristics are approximations and averages. The field observations reported herein are largely based on observations made from January through May 2018 on 5-year old plants located in an advanced trial plot near Interlachen, Fla., as well as observations made in an advanced trial in Manor, Ga. Laboratory analysis of fruit characteristics were done in Grand Junction, Mich. The bushes in the advanced trials were propagated from the original bush selected near Interlachen, Fla. and have retained the characteristics of the original selection. Cultivar name: 'BB05-35FL-10'.

Classification:

*Family*.—Ericaceae.

*Botanical name*.—*Vaccinium* (complex ancestry, based largely on *V. corymbosum, V. ashei*, and *V. darrowii*, with a limited contribution from *V. tenellum* and *V. fuscatum*).

*Common name*.—Blueberry.

Parentage:

*Female parent*.—'Star', U.S. Plant Pat. No. 10,675. Compared to 'Star', for 'BB05-35FL-10' the mean date of 50% anthesis is 5 days earlier and 'Star', the mean date of 50% ripe fruit is 5 days earlier, and 'BB05-35FL-10' has a much heavier berry weight (2.9 grams/berry vs. 1.9 grams/berry). In addition, the summer twig color of 'BB05-35FL-10' is Pantone Herbal Garden 15-0336 vs. Pantone Golden Green 16-07 for 'Star'.

*Male parent*.—'Emerald', U.S. Plant Pat. No. 12,165. Compared to 'Emerald', for 'BB05-35FL-10' the mean date of 50% anthesis is 5 days earlier, and the mean date of 50% ripe fruit is 5 days earlier. The ripe fruit color of for 'BB05-35FL-10' is different, Pantone Quarry 15-4305 vs. Pantone Gull 17-3802 for 'Emerald'. 'BB05-35FL-10' originated from the cross of 'Star' x 'Emerald' made in a greenhouse in South Haven, Mich. in 2005. Seeds of this cross were collected, germinated and grown as seedlings near Holland, Mich. in a greenhouse for 18 months and then shipped and planted in a seedling observation plot near Interlachen, Fla. in 2006. 'BB05-35FL-10' was first selected in May 2008 for its interesting morphological characteristics of very large fruit, yield and fruit quality. 'BB05-35FL-10' was asexually propagated in Interlachen, Fla., by cuttings in 2008 and plants were planted in advanced trials in Interlachen, Fla. and Manor, Ga. 'BB05-35FL-10' has been asexually propagated several times in the succeeding years by cuttings and tissue culture and all of the propagated plants have retained the original characteristics.

Growing location(s) for the observations herein: Interlachen, Fla. and Manor, Ga.; observations made from January-May 2018 on 5-year old plants.

'BB05-35FL-10' is a new and distinct low chill tetraploid, Southern highbush blueberry (*Vaccinium*) variety of complex ancestry, based largely on *V. corymbosum, V. ashei*, and *V. darrowii*, with a limited contribution from *V. tenellum* and *V. fuscatum*. 'BB05-35FL-10' is a very productive cultivar with early season maturity and excellent fresh market fruit quality with mechanical harvest capability. Potential areas of adaptation include northern Florida and southern Georgia, California, central Chile, and Peru. Plants of 'BB05-35FL-10' are very vigorous and medium upright with a medium number of upright canes and lateral branches. Bush crown size is medium and leafing and growth are excellent. Flowering is early in northern Florida and southern Georgia, USA, and may require frost protection for successful pollination. Flowering and leafing are synchronous. The fruit is born on loose pedicels and is well presented on the branch tips. Fruit color is medium blue; berries are very large in size, 18 mm or larger, and have a small and dry pedicel scar. The berries are firm and medium crunchy in texture with a pleasing balanced flavor of sweetness and acidity and have storage ability of two to three weeks. In general, the productivity has been outstanding in Florida, Georgia USA, and Chile with high yields.

Color description reference: The Pantone Book of Color, Eisemann and Herbert, Hall"y N. Abrams, Inc. Publishers, New York, ISBN 0-8109-3711-5, 1990.

Morphological characteristics referenced: Plant Systematics, Jones and Luchsinger, 2 Ed., McGraw Hill, New York, ISBN 0-07-032796-3, 1986.

Firmness readings: Bio Works FirmTec2, Wamena, Kans.

Device used to measure Soluble Solids (SS-Brix°), Titratable acidity (TA), pH: PAL-BX/Acid 7, Atago USA, Inc., Bellevue, Wash.

Average size information:

*General description*.—Medium large bush, medium upright bush shape, 5-year old plant averages 115 cm in height, 75 cm width, height/width ratio 1.5:1.

*Growth*.—Very good growth, leaving and vigor.

*Productivity*.—Excellent.

*Cold hardiness*.—Leaf and flower buds −5° C., open flowers and fruit −2°.

Specific features of the variety:

Plant:

*Growth habit*.—Medium upright.

*Plant width*.—75 cm at mid-bush.

*Plant height*.—5-year-old bush (Interlachen, Fla.) 115 cm.

*Spread*.—Canopy 85 cm.

*Productivity*.—7-8 pounds per bush at maturity.

*Cold hardiness/tolerance*.—Leaf and flower beds −5° C. and fruit −2° C.

*Chilling requirement*.—200-300 hours below 7° C.

*Canes*.—Moderately branched, average 6 mature canes per bush, 60-75 cm in length, medium number of laterals.

*Mature cane color and texture*.—Pantone Gray Sand 13-1010, rough texture.

*Fruiting wood*.—Smooth texture. Immature winter color — Pantone Russet Brown 19-1338. Immature summer color — Pantone Herbal Garden 15-0336. Internode length: range 20 mm-28 mm, width 7 mm.

*Mature canes*.—Oval shape, 15 mm in width.

*Time of beginning of leaf bud burst*.—January 25, Interlachen, Fla.

*Time of beginning of flowering*.—February 4, Interlachen, Fla.

*Time of beginning fruit ripening*.—April 10, Interlachen, Fla.

*Disease resistance/susceptibility*.—None claimed.

Foliage:

*Leaf color*.—Upper — Pantone Artichoke Green 18-0125. Lower — Pantone Forest Green 17-0230.

*Leaf arrangement*.—Simple alternate.

*Leaf margins*.—Entire.

*Leaf venation*.—Pinnate.

*Leaf apices*.—Acute.

*Leaf bases*.—Acute.

*Vein and petiole coloration*.—Pantone Herbal Garden 15-0336.

*Petiole length*.—4 mm.

Leaf dimensions:

*Overall shape*.—Elliptic.

*Length*.—Range 54-64 mm, averages 60 mm.

*Width*.—27-32 mm, averages 29 mm.

*Leaf margins*.—Entire.

*Leaf surface*.—Smooth upper and lower surfaces, no pubescence or nectaries observed.

Flower:

*Flower shape*.—Urceolate.

*Flower bud number*.—Medium high.

*Flowers per cluster*.—Averages 7.

*Flower fragrance*.—Light floral.

*Corolla color*.—Pantone Antique White 11-0105.

*Corolla length*.—11 mm.

*Corolla aperture width*.—5 mm.

*Flower peduncle*.—5 mm.

*Flower peduncle diameter*.—1 mm.

*Flower peduncle texture*.—Smooth.

*Flower peduncle color*.—Pantone Grasshopper 18-0332.

*Flower pedicel*.—2.5 mm.

*Flower pedicel diameter*.—1 mm.

*Flower pedicel texture*.—Smooth.

*Flower pedicel color*.—Pantone Grasshopper 18-0332.

*Calyx* (*with sepals*).—2 mm.

*Calyx color*.—Pantone Herbal Garden 15-0336.

*Stamen*.—Length: 6 mm. Number per flower: 10. Filament color: Pantone Herbal Garden 15-0336. Style: 8 mm from ovary to stigma tip. Color: Pantone Beechnut 14-0425.

*Pistil length*.—9 mm, even with the top of the corolla.

*Pistil color*.—Pantone Herbal Garden 15-0336.

*Ovary color*.—Pantone Herbal Garden 15-0336.

*Anther*.—Length: 4 mm. Number: 10. Color: Pantone Buckskin 16-1342.

*Pollen*.—Abundance: Medium high. Color: Pantone Winter White 11-0507.

Fruit:

*Date of* 50% *maturity*.—April 15 Interlachen, Fla.

*Yield*.—7-8 pounds per bush at maturity.

*Berry color*.—With wax: Pantone Quarry 15-4305. With wax removed: Pantone Majolica Blue 19-4125.

*Berry flesh color*.—Pantone Frozen Dew 13-0513.

*Berry surface wax abundance*.—Medium, moderately persistent.

*Berry weight*.—Average 2.9 grams.

*Berry size*.—Width: 18 mm, Height: 15 mm, Aspect (H/W) — 0.08.

*Berry shape*.—Oblate.

*Fruit pedicel scar*.—Very small, dry, 1 mm in diameter, 1 mm depth.

*Berry firmness*.—Very good, Firm Tec score: 192 $g/mm^2$.

*Berry sweetness*.—Medium, Brix° — 11.4.

*Berry acidity*.—Medium, Titratable acidity — 0.54.

*Berry flavor and texture*.—Very good and balanced, juicy, firm with medium crunchy texture.

*Storage quality*.—Very good, storage of 2-3 weeks in ambient cold storage with little decay.

*Suitability for mechanical harvesting*.—Bush shape, crown size, berry detachment and firmness are good for mechanical harvest potential.

*Uses*.—Fresh market, processed into jams, puree and yogurt.

Seed:

*Seed abundance in fruit*.—Medium number, average 8-10 per fruit.

*Seed color*.—Pantone Clay 15-1231.

*Seed dry weight*.—N/A.

*Seed size*.—1 mm length, 0.5 mm width.

What is claimed is:

1. A new and distinct cultivar of Blueberry plant named 'BB05-35FL-10' as described and shown herein.

* * * * *